United States Patent [19]

DonMicheal et al.

[11] Patent Number: 4,870,953
[45] Date of Patent: Oct. 3, 1989

[54] INTRAVASCULAR ULTRASONIC CATHETER/PROBE AND METHOD FOR TREATING INTRAVASCULAR BLOCKAGE

[76] Inventors: T. Anthony DonMicheal, 309 Panorama Dr., Bakersfield, Calif. 93305; Robert J. Siegel, 2304 Strongs Dr., Venice, Calif. 90291; Eugene A. DeCastro, 112 Hunter St., Jamestown, N.Y. 14701

[21] Appl. No.: 120,390

[22] Filed: Nov. 13, 1987

[51] Int. Cl.⁴ .......................................... A61H 23/00
[52] U.S. Cl. .................................. 128/24 A; 128/328; 128/786
[58] Field of Search ................ 128/24 A, 24 R, 328, 128/786, 660.01

[56] References Cited

U.S. PATENT DOCUMENTS

| | | | |
|---|---|---|---|
| 3,228,400 | 1/1966 | Armas | 128/401 |
| 3,369,549 | 2/1968 | Armas | 128/401 |
| 3,496,942 | 2/1970 | Shipley | 128/401 |
| 3,517,665 | 6/1970 | Sheldon | 128/24 A |
| 3,526,219 | 9/1970 | Balamuth | 128/2 |
| 3,589,363 | 6/1971 | Banko | 128/276 |
| 3,830,240 | 8/1974 | Antonevich | 128/24 A |
| 3,861,391 | 1/1975 | Antonevich, et al. | 128/328 |
| 4,375,220 | 3/1983 | Matoia | 128/401 |
| 4,431,006 | 2/1984 | Trimmer et al. | 128/24 A |
| 4,602,633 | 7/1986 | Goodfriend et al. | 128/328 |
| 4,643,186 | 2/1987 | Rosen et al. | 128/784 |
| 4,676,258 | 6/1987 | Imokuchi et al. | 128/401 |
| 4,698,058 | 10/1987 | Greenfeld et al. | 128/24 A |
| 4,748,971 | 6/1988 | Borodulin | 128/24 A |
| 4,754,752 | 7/1988 | Ginsburg et al. | 128/401 |

FOREIGN PATENT DOCUMENTS

| | | | |
|---|---|---|---|
| 0253677 | 1/1988 | European Pat. Off. | 128/401 |
| 8701276 | 6/1986 | PCT Int'l Appl. | 128/24 A |

*Primary Examiner*—Edgar S. Burr
*Assistant Examiner*—Huong Q. Pham
*Attorney, Agent, or Firm*—Spensley, Horn, Jubas & Lubitz

[57] ABSTRACT

Apparatus and method are disclosed for treating atherosclerotic plaque and thromboses by the application of ultrasonic energy to a site of intravascular blockage. The ultrasonic apparatus includes a solid wire probe having a bulbous tip at one end and coupled to an ultrasonic energy source at the other end, the probe being carried within a hollow catheter. The catheter and probe are inserted into a blood vessel and are advanced to the site of a stenosis, where the probe is extended from the catheter and caused to vibrate ultrasonically, resulting in the destruction of the arterial plaque. The ultrasonic apparatus includes a fitting for delivering a radiographic contrast solution to the probe tip by flowing the solution into the catheter, the contrast fluid being released into the blood vessel to assist in positioning the apparatus and determining the effectiveness of treatment. A physiologic solution may also be carried to the probe tip by flowing the solution through the catheter, thereby controlling the temperature of the probe tip during the procedure.

43 Claims, 3 Drawing Sheets

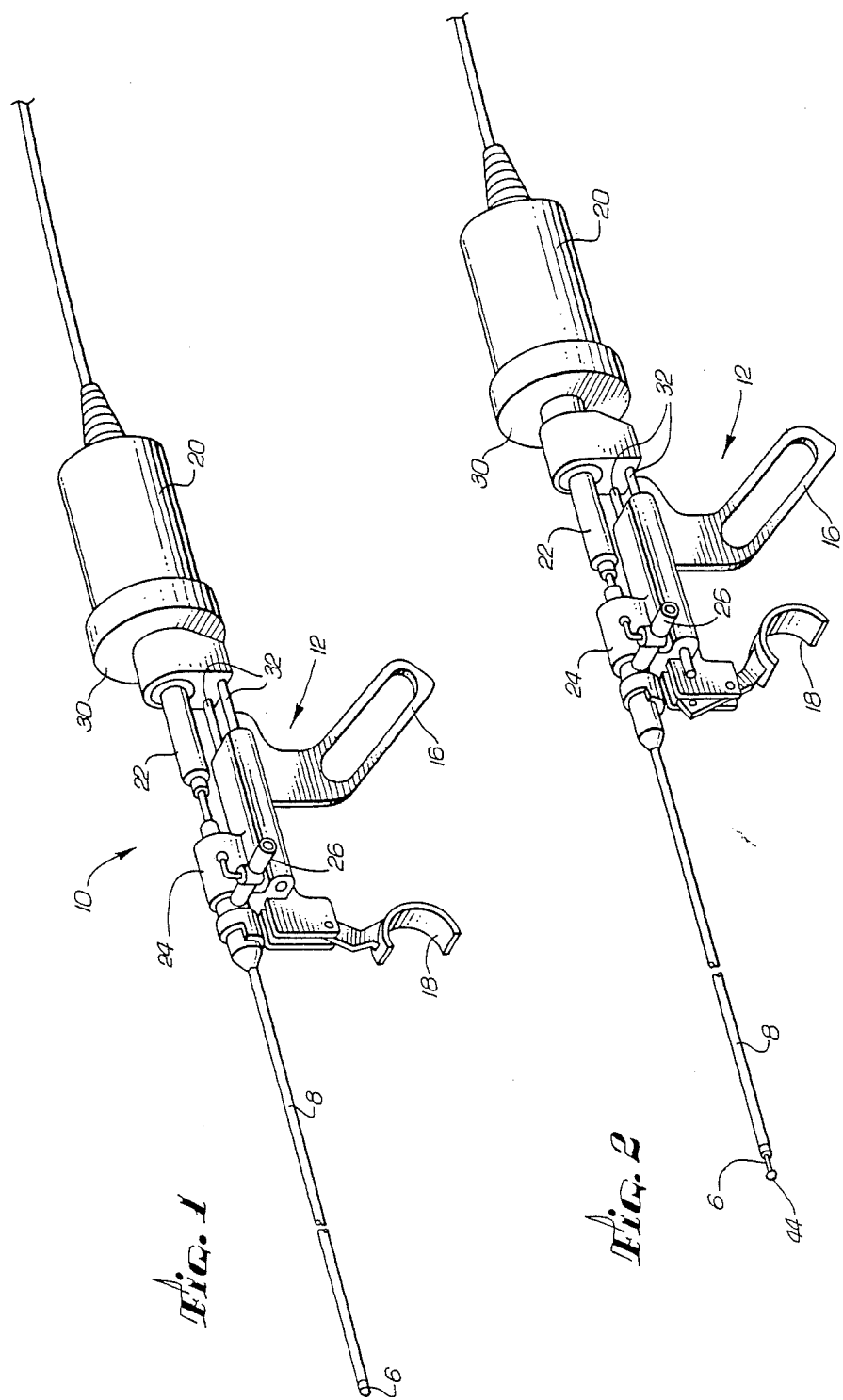

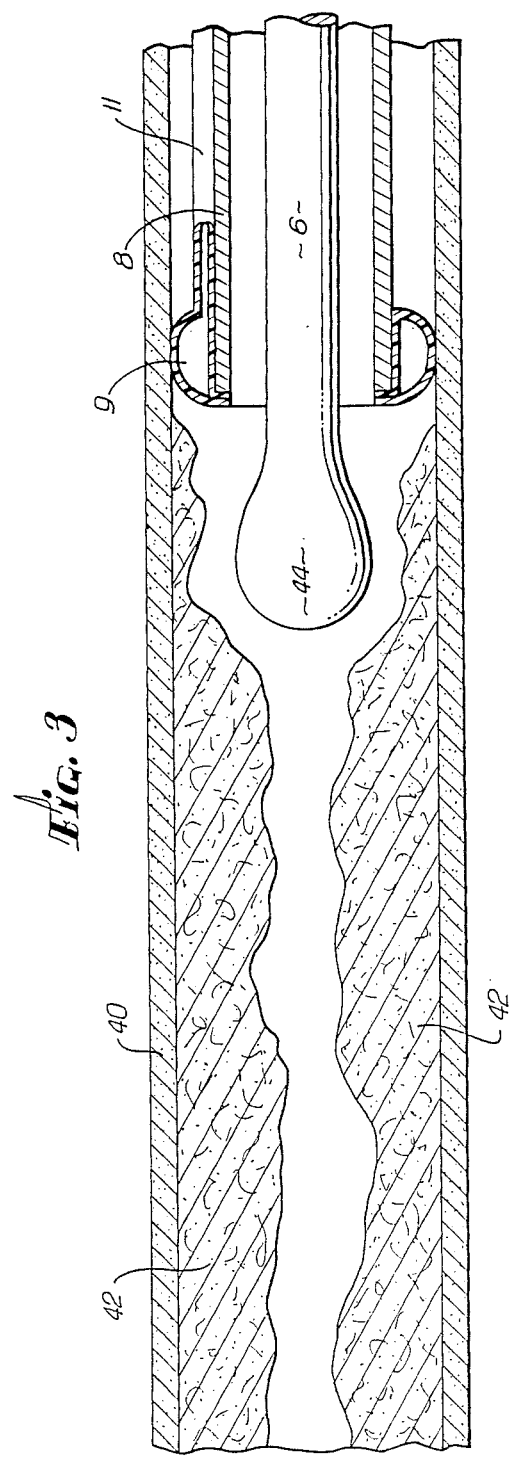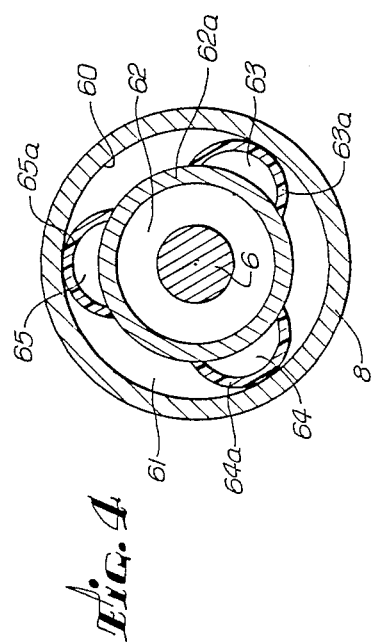

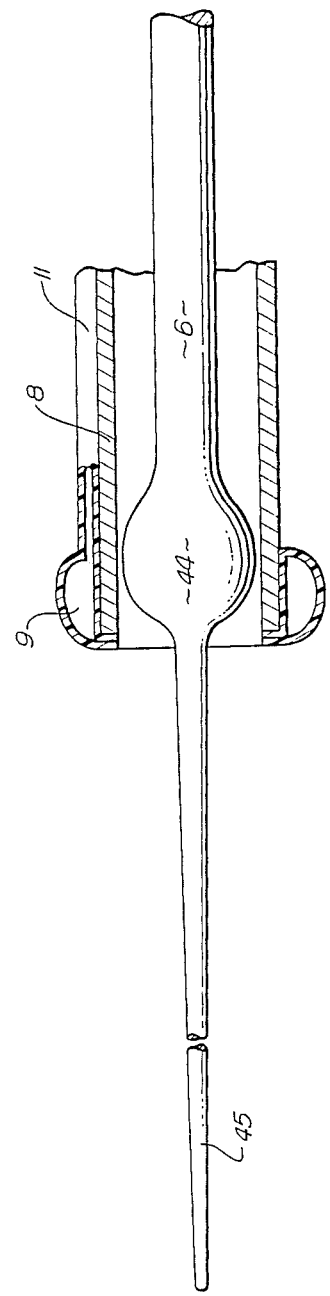

INTRAVASCULAR ULTRASONIC CATHETER/PROBE AND METHOD FOR TREATING INTRAVASCULAR BLOCKAGE

BACKGROUND OF THE INVENTION

1. Field of the Invention

This invention relates to therapeutic treatment for the removal of intravascular blockage due to atherosclerotic plaque and intravascular blood clots and, more particularly, to a method and apparatus for the removal of atherosclerotic plaque and blood clots in blood vessels by the use of ultrasonic energy.

2. Description of the Related Art

For proper health, the arteries must have sufficient elasticity to expand with each heartbeat and to withstand the high pressures of arterial blood flow. When cholesterol, fibrous material, and other substances coat the inner surface of arteries, there can be a severe loss in blood vessel elasticity. This condition is commonly referred to as atherosclerosis. In addition to cholesterol and fibrous materials, calcium deposits may accumulate that can further reduce the elasticity of the blood vessel and can cause the accumulated deposits to become hard.

The deposits are most frequently associated with the blood vessels supplying the heart, but the deposits may occur elsewhere in the body. These deposits, which are generally referred to as plaque, accumulate at one location and drastically narrow the bore of the artery, thus restricting and even totally blocking the flow of blood. Plaque has a thick, viscous consistency. The site of accumulated deposits that constrict the blood vessel is referred to as a stenosis while a total blockage is referred to as an occlusion. Similarly, a blood clot is often associated with the blood vessels supplying the heart, but may occur elsewhere in the body. An intravascular blood clot is generally referred to as a thrombosis.

Many different techniques and devices have been used in the treatment of atherosclerosis and thromboses. Each of the techniques suffers from deficiencies that make an alternative procedure desirable. These techniques include arterial bypass surgery, endarterectomy, balloon angioplasty, applications of laser technology, mechanical and electrical drills, and other surgical techniques and tools for the removal of the deposits.

Arterial bypass surgery involves the bypass of the narrowed or occluded arterial segment by using a synthetic conduit or an arterial or venous graft to carry blood past the arterial obstruction. Arterial bypass surgery requires surgery, with the attendant risks of surgery and general anesthesia, problems of wound healing and infection, post-operative complications, and the problem of post-operative graft closure.

Endarterectomy also requires direct surgery, but further requires that the blocked blood vessel itself be opened and the blockage removed. That is, the blood vessel is exposed during surgery, the vessel is slit open along the blocked portion, and the blockage is manually removed by the physician. The slit must then be sealed up so that blood may once again flow through the vessel. Thus, this technique is in many ways more invasive than bypass surgery and includes all of its potential shortcomings.

Balloon angioplasty is a recent development that involves the insertion of a catheter having a circumferential balloon attached at its distal end. A thin, flexible guide wire is first inserted in the blood vessel and is advanced to the site of a stenosis. A catheter is then slipped over the guide wire and is advanced in the blood vessel along the length of the wire. Once the catheter is at the stenosis, the balloon is inflated and thereby dilates the stenotic arterial segments. This stretches the artery and may obviate the need for arterial bypass operations. The limitations of balloon angioplasty include arterial dissection, bleeding, and re-occlusion. Furthermore, most total stenoses or occlusions and totally calcified blockages cannot be treated by balloon angioplasty techniques, as balloon angioplasty does not destroy or pulverize arterial plaque or clots. In fact, very few non-surgical techniques are capable of opening up a totally calcified blockage. A "hot-tip" catheter, for example, can be used for most fibrous blockages but cannot be used for totally calcified blockages. A hot-tip catheter also has an increased risk of perforation.

Efforts are also under way to apply laser technology to dissolve or vaporize plaque. There currently are no laser techniques in widespread use. Laser techniques, however, have a high damage potential related to perforation of the blood vessel. In such a case, direct visual observation can be extremely important in avoiding damage to healthy tissue.

Drill techniques typically employ a stiff, threaded probe that rotates and thereby drills or reams out the plaque. These techniques also present a high damage potential, primarily due to perforation, and therefore direct visual observation of the site may be necessary. For direct visual observation, it may be necessary to use angioscopy to insert a fiber optic probe into the blood vessel, further complicating the treatment process. Angioscopy involves the insertion of an angioscope, or fiber optic probe, into the blood vessel for visual inspection of the treatment site. Alternatively, direct surgical techniques would be necessary. Thus, there is a need for a device that will dissolve or pulverize atherosclerotic plaque and intravascular obstructions without these dangerous and cumbersome complications.

The use of ultrasonic energy for the destruction of plaque has been suggested, but prior techniques and devices still suffer from deficiencies and there have been no successful applications of the technology in treatment. For example, U.S. Pat. No. 3,565.062 to Kuris utilizes a catheter inserted into a blood vessel and requires a procedure in which the blocked artery is surgically exposed. Thus, many of the potential problems of arterial bypass surgery are present. In addition, a hollow vibrating probe is provided in conjunction with a catheter having slots for catching strips of plaque to be shaved off. The apparatus and accompanying procedure are quite involved and time-consuming, and require much manipulation.

The device of U.S. Pat. No. 3,526,219 to Balamuth utilizes ultrasonic energy but is used for the removal of tumors, warts, moles, skin cancer, and others from the surface of skin tissue. The device has no application to the interior of blood vessels. The device of U.S. Pat. No. 3,433,226 to Boyd relates to a catheter that vibrates at an ultrasonic resonant frequency to destroy plaque. Because the catheter itself vibrates adjacent to the blood vessel wall, and is advanced in the blood vessel for destruction of the stenosis, there is a danger of perforation of the vessel wall during application of ultrasonic energy. Thus, these previous ultrasonic methods of treating plaque still include many undesirable complications and dangers.

SUMMARY OF THE INVENTION

The present invention provides a method and apparatus for removing intravascular blockage due to atherosclerosis or blood clots. Some of the advantages of the apparatus of the present invention and methods of use thereof are rapid destruction of arterial stenoses (on the order of seconds rather than minutes, as with other techniques), low risk of rupture of arterial walls, lack of significant damage to normal healthy vessels, the ability to open blood vessels that are totally occluded by atherosclerotic fibrous plaque and/or calcified plaque, the ability to dissolve occlusive and non-occlusive clots within blood vessels, and the ability to perform the procedure at the time of a diagnostic angiogram, thus obviating the need for surgery. In addition, direct visual observation of the treatment site, and therefore angioscope (a fiber optic probe inserted within a catheter), is not necessary for the procedure.

The apparatus of the present invention comprises an elongated, flexible wire probe having a bulbous tip and carried within a catheter or sheath made of or coated with a plastic or other friction-reducing material. The end of the probe having the bulbous tip is placed in contact with an intravascular blockage and the other end of the probe is attached to an ultrasonic power source. The bulbous tip reduces the rise of blood vessel perforation as compared with the techniques discussed above. The probe carries ultrasonic energy from the ultrasonic power source to the site of intravascular blockage. Unlike most ultrasonic catheter/probe combinations, the flexible probe is made to vibrate transversely as well as forward and backward. The catheter may also be connected to the ultrasonic power source but does not vibrate and is used only to act as a conduit for placement of the flexible probe at the site of blockage and for carrying radiographic contrast fluid into the blood vessel. The catheter also may be provided with an annular inflatable cuff at its distal end for centering the catheter/probe and sealing off the treatment site.

Conventional angiography insertion techniques can be used to insert the apparatus of the present invention into the blood vessel, thus eliminating surgical procedures. After the catheter and probe are inserted in the blood vessel, they are advanced upstream of blood flow to the site of blockage. The advantage of the angiographic insertion technique is that surgery is not required and the patient is not under general anesthesia. The treatment method and apparatus of the present invention also may be used with insertion techniques besides that of the angiogram in order to gain access to the blood vessel interior. For example, the apparatus may be used along with direct surgery techniques for more effective removal of intravascular blockages.

Once the apparatus of the present invention is inserted in the blood vessel, a radiographic contrast fluid that appears nearly opaque in an x-ray image is infused in the catheter, which is otherwise nearly transparent in an x-ray image. The contrast fluid may be released in the blood vessel in controlled quantities, so as to fill the blood vessel and clearly expose it to observation in real-time on an x-ray video image monitor, such as a fluoroscope. In this way, the artery and the progress of the catheter and probe in the artery may be observed. Thus, direct visual observation of the artery as the catheter moves along in the artery is probably unnecessary and the fiber optic catheter normally used with angioscopy techniques is probably not needed. Nevertheless, direct visual observation may be used along with the disclosed method and apparatus, if desired.

If the catheter is provided with a cuff or circumferential balloon at the end of the catheter, the balloon may be inflated to contact the blood vessel wall once the catheter is at the treatment site, thereby centering the catheter within the blood vessel and blocking off the treatment site. With the catheter centered, the probe is less likely to veer off-axis within the blood vessel when it is extended, and is more likely to remain equidistant from the vessel wall during extension from the catheter and during ultrasonic vibration. This further reduces the chances of vessel perforation and damage to healthy tissue. Blocking off the treatment site aids in aspiration of most if not all particles of debris and helps to prevent particles from escaping backward into the bloodstream.

When the catheter is at the appropriate arterial location, the probe may be advanced outside of the catheter to come into contact with the plaque or thrombosis. At the same time, the ultrasonic power source may be activated to supply continuous or pulsed ultrasonic energy to the mass of plaque or thrombosis through the probe tip. Preferably, the ultrasonic energy is pulsed at 20 millisecond intervals, being on for 20 msec. and off for 20 msec. This prevents the probe tip from becoming heated. Since a hot probe is more likely to perforate a vessel wall than a cool probe, this helps to further reduce the chances of perforation.

More contrast fluid or contrast fluid of a higher concentration may be let into the artery once ultrasonic treatment begins and then the progress of the contrast fluid in the artery may be viewed in real-time on an x-ray image video monitor screen. This allows the progress of the treatment in removing the stenosis to be observed by noting the flow of radiographic contrast fluid. If the contrast fluid does not move along in the blood vessel, the occlusion is still present. Again, direct visual observation of the treatment site is ordinarily unnecessary.

Physiologic saline or other physiologic solutions may also be inserted into the hollow catheter to flow around the probe to the site of the arterial stenosis. Alternatively, the catheter may be provided with multiple lumens, or passageways, for the passage of fluids to and from the treatment site. In this way, the temperature of the probe tip may be further controlled during the application of ultrasonic energy by varying the rate of infusion of the physiologic solution. This prevents undue heating of the probe tip, which could damage the adjacent healthy tissues. Thus, the present invention contemplates the use of a catheter with a single passageway or a catheter having multiple lumens for all of the various fluids.

BRIEF DESCRIPTION OF THE DRAWINGS

The invention will now be described with reference to the accompanying drawings, in which like reference numerals refer to like elements, wherein:

FIG. 1 is a perspective view of an ultrasonic device incorporating the catheter and probe of the present invention with the probe retracted into the catheter;

FIG. 2 is a perspective view of an ultrasonic device incorporating the catheter and probe of the present invention showing the probe extended from the catheter;

FIG. 3 is a sectional side view of an occluded blood vessel illustrating the breakup of plaque in conjunction with use of the present invention;

FIG. 4 is a sectional view looking into a catheter of the present invention having multiple lumens for the passage of the probe, the radiographic contrast fluid, and suction of plaque debris; and FIG. 5 is a sectional side view of the catheter and probe tip of the present invention illustrating the flexible probe extension.

DESCRIPTION OF THE DRAWINGS

The following description is of the best presently contemplated mode of carrying out the invention. This description is made for the purpose of illustrating the general principles of the invention and is not to be taken in a limiting sense. The scope of the invention is best determined by reference to the appended claims. "Artery" and "blood vessel" are used interchangeably to refer to blood vessels generally. Although the discussion refers primarily to the treatment of atherosclerosis, it is to be understood that the techniques and devices discussed also apply to the treatment of blood clots as well.

FIG. 1 shows a perspective view of a catheter 8 and probe 6 attached to an ultrasonic power source 10 generating ultrasonic vibrations that are transmitted through the probe. The particular ultrasonic power source 10 illustrated in FIG. 1 may be of the type commonly used in conjunction with a probe inserted into the urethra for the treatment of calcified stones in the urinary tract. The exact configuration and method of generating ultrasonic vibrations is not critical to the present invention. Either continuous ultrasonic energy or pulsed ultrasonic energy may be used.

The ultrasonic power source includes a support stock 12 which has a support rack 14, an integral grip 16, and a trigger 18. Attached at one end of the power source is an ultrasonic vibration generator 20, to which is connected one end of the metal probe 6. The vibration generator 20 uses electrical energy to produce ultrasonic vibrations by, for example, vibrating a crystal at ultrasonic frequencies. Connecting the metal probe 6 to the vibration generator 20 allows the ultrasonic vibrations of the crystal to be transmitted down the length of the probe. The generator 20 is attached to a mounting bracket 30 having two rods 32 and 34 that are inserted into the stock 12. The probe is coupled to the ultrasonic vibration generator 20 through a vibration fitting 22 that is part of the mounting bracket 30.

The ultrasonic power source preferably makes the probe vibrate transversely as well as backward and forward. The dual transverse and longitudinal motion increases the efficiency of the ultrasonic energy in destroying the intravascular blockage. In accordance with techniques known in the art, the length of the probe may be selected for maximum energy efficiency and effectiveness of transverse and longitudinal probe movement. Specifically, the length of the probe is selected so as to be an acoustical length that is a whole number multiple of one-half the wavelength of the ultrasonic frequency in the material of which the probe is made, with the bulbous tip located at an antinode of the probe length. The antinodal point is the point at which longitudinal and transverse motions of the probe are at a peak, and therefore the probe tip will undergo both longitudinal and transverse motion. The movement of the probe has a peak-to-peak magnitude of approximately 40 microns.

The ultrasonic movement of the probe serves to break up and dissolve the plaque in a chipping or beating action. In addition, movement of the probe creates bubbles and turbulence. The turbulence creates a cavitation action or increase in fluid pressure at the treatment site on the order of 2 to 3 atmospheres. This type of cavitation action works in concert with the chipping action to further break up the particles of plaque.

The probe 6 is preferably constructed of flexible metal wire, such as a cobalt nickel alloy, and is carried in the catheter 8 such that the distal end of the probe is slightly recessed within the catheter. The probe passes through an irrigation fitting 24 that is attached to the stock 12. Attached to the fitting 24 is the catheter or sheath 8 that may be constructed, for example, of plastic. The irrigation fitting 24 includes a fluid conduit 26. The conduit communicates with the catheter via an internal passageway (not illustrated) and in this way a radiographic contrast fluid may be introduced through the conduit 26 into the catheter. The contrast fluid presents a distinct image of the probe and blockage in an x-ray image, depending on concentration, and allows the treating physician to observe the location of the catheter and probe in the blood vessel while also monitoring the progress of the ultrasonic treatment in destroying the occlusion and improving the flow of blood in the blood vessel. The fluid conduit also may be used for aspiration (suction) of debris from the treatment site. Alternatively, more than one fluid conduit may be provided. For example, one conduit may be used for aspiration while another conduit may be used for contrast fluid.

FIG. 2 shows a perspective view of the ultrasonic device 10 illustrating the probe 6 extended from the catheter 8. The ultrasonic vibration generator 20 is attached to a bracket 30 having two rods 32 and 34, which fit into cylindrical openings in the support stock 12. The forward end of the bracket 30 is coupled to the trigger 18 such that pulling back on the trigger pulls the bracket 30 forward, carrying the vibration generator 20 with it. Since the probe 6 is attached to the vibration generator 20 via the vibration fitting 22, pulling on the trigger causes the probe to slide forward with the generator 20. Because the catheter 8 is attached to the fitting 24, which is attached to the stock 12 and does not move, the catheter 8 remains stationary when the probe 6 moves forward. The probe, which is normally coextensive with or slightly recessed from the end of the catheter 8, slides within the catheter and is thereby extended from the end of the catheter.

FIG. 3 shows a sectional side view of the present invention in place in an occluded blood vessel. The interior surface of the vessel wall 40 is shown with a mass of plaque 42 deposited hereon. The catheter 8 and probe 6 have been inserted upstream into the blood vessel and are located adjacent to the occluded mass 42. The metal probe 6 has been extended from the catheter 8 so as to make contact with the plaque. FIG. 3 shows that the tip 44 of the probe has a bulbous shape. This shape has been found to result in the rapid destruction of atherosclerotic plaque by efficiently transferring the ultrasonic energy while being free of any tendency to poking, tearing or perforating the healthy blood vessel wall. The bulbous tip 44 of the probe is preferably slightly less in diameter than the inside diameter of the catheter, and therefore can be easily carried in the catheter to the treatment site. Because the probe is carried within a catheter to the sight of the stenosis, the probe needn't be rigid or stiff enough to be advanced independently in the blood vessel. Thus, the probe can be made flexible enough to prevent perforation of the blood vessel during treatment.

The probe vibrates generally at a fixed frequency, that frequency being in the range of 20,000 to 27,000 Hz. The vibration may be steady and continuous or it may be pulsed. Preferably, the pulsing has a 20 msec. cycle time, being on for 20 msec. and then off for 20 msec. The energy applied, in terms of watts, may also be varied. As the probe tip 44 vibrates ultrasonically, the tip 44 tends to become heated. As the probe vibrates it breaks up and pulverizes the plaque or clot but, if uncontrolled, the temperature of the tip could damage the adjacent blood vessel wall 40. Pulsing the vibration action, rather than using continuous energy, may help to reduce and control the tip temperature. From the relative size of the tip 44 and catheter 8 illustrated in FIG. 3, it is apparent that there is a space between the catheter wall 8 and the probe tip 44, as well as between the catheter wall and the metal probe 6. Physiologic solution introduced through the conduit 26 of the ultrasonic energy source can flow in this space through the catheter and directly to the tip 44 of the probe, thereby cooling the probe tip and providing a temperature regulating function. The arrows 46 show that the space between the probe and catheter can be used for the flow of fluid down the catheter and also for the aspiration of particles up the catheter.

The catheter 8 may be provided with a cuff or annular balloon 9 around its outer circumference near its distal end. A conduit 11 may be provided along the outside of the catheter or, alternatively, within the catheter or within the wall of the catheter, so as to provide air or fluid into the cuff and thereby inflate it. The cuff would remain deflated during the insertion procedure, and would be inflated once the catheter was located at the treatment site. FIG. 3 shows the cuff 9 inflated out to the vessel wall 40, thereby centering the catheter 8 in the blood vessel and blocking off the treatment site. By centering the catheter, the probe 6 is also centered in the blood vessel. This helps to ensure that the probe will not veer off from the center axis of the blood vessel toward the vessel wall once the probe is extended from the catheter, and prevents the probe from perforating the vessel wall. Blocking off the treatment site also helps to prevent large debris particles from travelling backward in the blood vessel and helps to contain the radiographic contrast fluid at the treatment site.

FIG. 4 shows a sectional view looking up a catheter 60 having multiple passageways or lumens 61, 62, 63, 64, and 65. Each of the passageways can be used for transporting various fluids to and from the treatment site. A circular central passageway 62 is preferably provided for passage of the probe 6, so that the probe is more likely to stay centered in the blood vessel and reduce the chance of perforation. An inner wall 62a forms the central passageway 62. Placed around the central passageway between it and the catheter interior wall surface 60 are the passageways 63, 64, and 65 having half-circle or semi-circular cross section, each passageway being formed by a wall 63a, 64a, and 65a, respectively. One passageway 63 may be used for carrying the radiographic contrast fluid, another passageway 64 may be used for suction of plaque debris, and a third passageway 65 may be used for infusing physiologic solution. Other passageways may also be provided, as desired. Thus, the treatment site may be simultaneously flushed and aspirated by the passageways. The cross-sectional shape of the lumens may be of any shape desired and are not limited to semicircular shapes.

The multiple lumens may be provided as shown in FIG. 4, with a central lumen within the catheter 8 and other lumens provided between the central lumen and interior wall of the catheter, or the multiple lumens may be provided by multiple concentric walls within the catheter 8. In either case, it is preferable that the central lumen or passageway in which the catheter is carried is also used for suction. This is desirable for two reasons. First, the central lumen is larger than the others, so that plaque debris will more easily be carried up the catheter without clogging if aspiration is performed. Second, the ultrasonic vibration travelling down the probe to the tip helps to further break up the debris being aspirated, further decreasing the likelihood of catheter clogging due to aspirated debris.

The multiple lumens will preferably be provided with an ultrasonic power source that includes multiple fluid conduits similar to the conduit 26. Preferably, each lumen will communicate with a different fluid conduit, although this is not essential. The exact manner of communication between the catheter passageways and the source of fluid or suction is not critical to the present invention.

The apparatus of the present invention may be inserted in a blood vessel in a manner similar to that used in taking an angiogram. In the angiographic procedure, a local anesthetic is applied at a convenient location of the patient, such as at an arm or leg, after which an incision is made through the skin and down to a blood vessel. A self-sealing sheath is inserted into the blood vessel at the incision. A catheter may then be inserted through the sheath and upstream into the blood vessel, and may be advanced in the vessel to the treatment site, such as a peripheral or coronary artery. This procedure allows the use of a simple local anesthetic rather than a surgical procedure with general anesthesia. The self-sealing sheath prevents blood from leaking back out from the blood vessel during the treatment. Thus, the patient's circulation is not interrupted.

Once introduced in the blood vessel, the catheter and probe may be passed to a particular site of interest by introducing radiographic contrast fluid into the blood vessel and viewing the real-time x-ray image of the catheter and probe within the artery on an x-ray monitor screen such as a fluoroscope. Preferably, the contrast fluid is released in the vessel at the time of catheter insertion to aid the physician in confirming that the catheter and probe are in the vessel and have not perforated the vessel wall.

The contrast fluid presents a distinct image of the probe and intravascular blockage on the fluoroscope. This allows the physician to determine the location of the catheter and probe at any instant in time and to confirm that the probe is still contained within the blood vessel and that no perforation has occurred. The progress of the treatment also may be viewed by observing the flow of contrast fluid from the catheter into the artery. The treatment site should be aspirated to clean it of debris and the cuff should be deflated. Then, if the contrast fluid does not move downstream from the catheter, the stenosis is still present. The faster the progress of contrast fluid, the greater the extent of plaque destruction.

In addition, a physiologic saline, anticoagulant or other physiologic solution may be introduced into the catheter, for example, to maintain the probe tip 44 at the desired temperature. The probe tip is heated during the application of ultrasonic energy and, depending on the procedure used, the healthy blood vessel tissue near the probe tip could become damaged if the tip temperature was not controlled. The physiologic solution may be inserted into the blood vessel by replacing the contrast fluid in the hollow catheter, or the solution may be inserted by using one of the passageways in a catheter with multiple lumens rather than a single hollow bore. Ordinarily, pulsing of the ultrasonic power and modulation of the power level will be sufficient to control the temperature of the probe tip and prevent damage to healthy tissue without physiologic solution.

FIG. 5 shows that the bulbous tip 44 or "ball point" end of the probe may be provided with a thin, very flexible extension 45 of 1 to 2 cm in length. The flexible extension is preferably not carried within the catheter. The floppy extension is flexible enough that it folds back on itself if it meets with an obstruction or vessel wall. In this way, the extension acts like a spring to divert the probe away from the wall or obstruction. The extension thereby helps to reduce the chance of blood vessel perforation while the probe and catheter are advanced in the blood vessel. FIG. 5 shows that the floppy extension 45 is smaller in diameter than that of the probe and the bulbous probe tip, and that the diameter of the probe tip 44 is slightly less in diameter than the inside diameter of the catheter. In the blood vessel, the extension 45 would be folded back on itself during the application of ultrasonic energy. The magnitude and velocity of movement of the extension 45 would thereby be less than that of the probe tip 44.

Thus, the procedure used with the apparatus of the present invention would be to first insert the self-sealing sheath and then the catheter carrying the probe into the blood vessel. Next, radiographic contrast fluid would be released through the catheter into the blood vessel, while observing the location of the catheter/probe combination on the x-ray or fluoroscope image. Once the end of the catheter is located at the site of occlusion, the trigger 18 may be pulled back so as to extend the probe 6 into the mass of plaque, whereupon ultrasonic energy may be applied through the probe 6 to break up and disintegrate the plaque. If the catheter is provided with a cuff, the cuff would be inflated prior to applying ultrasonic energy. It may be unnecessary to draw off the particles by aspiration, or suction. If suction is desired, a catheter with multiple lumens may be provided, one of the lumens being used for the suction removal of debris. Because of the reduced chance of perforation, and due to the fact that contrast fluid is delivered to the site of treatment, ordinarily it is not necessary to have direct visual observation of the treatment site.

The bulbous, solid probe allows efficient transfer of ultrasonic energy, flexible probe construction, and reduced chance of blood vessel perforation. The flexible probe and bulbous tip efficiently transfer ultrasonic energy to the mass of accumulated deposits, thereby breaking up and pulverizing the mass. The flexibility of the probe reduces the chance of perforating the blood vessel wall as the probe tip is advanced into the accumulated mass.

What is claimed is:

1. An ultrasonic apparatus for the treatment of a patient having blood vessels obstructed by deposits of atherosclerotic plaque or blood clots, comprising:
an ultrasonic energy source;
an elongated, solid, flexible probe having first and second ends and coupled at the first end to the ultrasonic energy source and having a tip at the second end, the probe length selected so as to provide both longitudinal and transverse motion of the probe tip, the probe tip having a blunt, rounded shape formed to be substantially free of any tendency to perforate a blood vessel and the probe having a degree of flexibility selected to prevent perforation of the blood vessel upon contact with the probe tip;
a hollow catheter for internally carrying a portion of the probe, the catheter having first and second ends, the tip of the probe having a diameter less than the internal diameter of the hollow catheter; and
means adapted to slide the probe within the catheter to extend the probe from the second end of the catheter into a mass of atherosclerotic plaque or blood clots.

2. An ultrasonic apparatus for the treatment of a patient having blood vessels obstructed by deposits of atherosclerotic plaque or blood clots, comprising:
an ultrasonic energy source;
an elongated, solid, flexible probe having first and second ends and coupled at the first end to the ultrasonic energy source and having a tip at the second end, the probe length selected so as to provide both longitudinal and transverse motion of the probe tip, the probe tip having a blunt, rounded shape formed to be substantially free of any tendency to perforate a blood vessel and the probe having a degree of flexibility selected to prevent perforation of the blood vessel upon contact with the probe tip; and
a hollow catheter having first and second ends, internally carrying a portion of the probe, the tip of the probe having a diameter less than the internal diameter of the hollow catheter, the second end of the probe adapted to be inserted into the blood vessel to be treated; the catheter having an inflatable annular balloon around the outer circumference of the second end of the catheter.

3. The ultrasonic apparatus of claim 1 wherein the probe tip is provided with a flexible extension approximately 2 cm in length along the longitudinal axis of the probe, the extension being flexible enough to fold back on itself when contacting the blood vessel wall.

4. The ultrasonic apparatus of claim 2 wherein the catheter has a plurality of internal passageways that extend along the length of the catheter.

5. The ultrasonic apparatus of claim 2 wherein the catheter has means for inflating the balloon after the second end of the catheter is in the blood vessel.

6. An apparatus for use with an ultrasonic energy source and capable of being advanced in a blood vessel to the site of a blockage due to atherosclerotic plaque or blood clot for the treatment of the blockage, comprising:
a flexible, elongated metal wire probe having one end adapted to be coupled to the ultrasonic energy source and having a tip at the other end, and the length of the probe being selected so that the probe length is an acoustical length of a whole number multiple of a one-half wavelength of the frequency of the ultrasonic energy source in the material of which the probe is constructed, with the tip of the probe located at an antinode of the probe length, the tip having a blunt, rounded shape formed to be substantially free of any tendency to perforate a blood vessel and the probe having a degree of flexibility selected to prevent perforation of the blood vessel upon contact with the probe tip;

a hollow catheter comprised of a flexible material having an inside diameter sufficient to internally carry the blunt, rounded tip of the probe, adapted to be inserted into the blood vessel at one end, and having an inflatable cuff at the inserted end that may be inflated to axially center the catheter and probe in the blood vessel; and means, coupled to the catheter, for introducing fluid into the blood vessel through the catheter.

7. A method of treating a patient suffering from partial or total blood vessel blockage due to the deposition of fibrous or calcified plaque or a blood clot on the blood vessel interior wall, the method comprising the steps of:

(a) providing an ultrasonic energy source; an elongated, hollow catheter; and an elongated, solid, flexible probe carried internally within the catheter;

(b) providing the probe with a blunt, rounded tip having a diameter less than the internal diameter of the hollow catheter and with a length that results in both longitudinal and transverse motion of the probe tip, the blunt, rounded tip being formed to be substantially free of any tendency to perforate a blood vessel and the probe having a degree of flexibility selected to prevent perforation of the blood vessel upon contact with the probe tip;

(c) attaching a first end of the catheter and probe to the ultrasonic energy source such that a second end of the probe is coextensive with a second end of the catheter;

(d) making an incision in the outer skin of the patient down to a blood vessel;

(e) introducing the catheter carrying the probe into the blood vessel and advancing the catheter and probe to the site of blockage by viewing a real-time x-ray image of the catheter and probe in the blood vessel;

(f) extending the probe from the end of the catheter and thereby making contact with the fibrous or calcified plaque or blood clot at the site of blockage; and (g) transmitting ultrasonic energy along the probe so as to vibrate the probe tip at ultrasonic frequencies in the longitudinal and transverse directions, thereby breaking up and pulverizing the blockage.

8. The method of claim 7 wherein the step (c) of advancing the catheter and probe to the site of an arterial blockage includes introducing a radiographic contrast fluid through the catheter and around the probe to the site of the blockage in the blood vessel and viewing the contrast fluid in real-time on an x-ray image.

9. The method of claim 8 further comprising the step of:

(f) viewing the flow of contrast fluid released from the catheter into the blood vessel after the transmission of ultrasonic energy to determine the extent of destruction of the arterial blockage.

10. The method of claim 7 further comprising the step of:

(f) supplying a physiologic fluid through the catheter to the site of arterial blockage to control the temperature of the probe tip while the ultrasonic energy is being applied.

11. The method of claim 7 further comprising the step of:

(f) removing plaque debris from the area of the treatment site by creating a suction through the catheter.

12. The method of claim 7 wherein the catheter has a plurality of internal passageways extending along its length, the method further comprising the step of:

(f) removing plaque debris from the area of the treatment site by creating a suction through one of the internal passageways.

13. The method of claim 7 wherein the catheter has an annular, inflatable cuff located around the outer circumference of the second end of the catheter; and the step (f) of the method further includes inflating the annular cuff, thereby blocking off the treatment site and centering the catheter in the blood vessel.

14. A method of treating a patient suffering from partial or total blockage of a blood vessel due to the deposition of fibrous or calcified plaque or a blood clot on the blood vessel interior wall, the method comprising the steps of:

(a) providing an ultrasonic apparatus comprising an ultrasonic energy source; an elongated, solid, flexible probe coupled at a first end to the ultrasonic energy source and having a tip at a second end; a hollow catheter for internally carrying a portion of the probe such that the catheter is adapted to be coupled at a first end to means for introducing fluid into the catheter and inserted at a second end of the catheter into the blood vessel to be treated, and means to slide the probe within the catheter and to extend the probe from the second end of the catheter into a mass of atherosclerotic plaque or blood clot;

(b) providing the probe tip with a blunt, rounded shape having a diameter less than the internal diameter of the hollow catheter and formed to be substantially free of any tendency to perforate a blood vessel and the probe having a degree of flexibility selected to prevent perforation of the blood vessel upon contact with the probe tip, and the probe is selected to have a length that results in both longitudinal and transverse motion at the tip;

(c) inserting the probe within the catheter and attaching the first end of the probe to the ultrasonic energy source such that the second end of the probe is coextensive with the second end of the catheter;

(d) making an incision in the outer skin of the patient down to a blood vessel and inserting a self-sealing sheath into the blood vessel;

(e) introducing the catheter carrying the probe through the self-sealing sheath and into the blood vessel, and advancing the catheter and probe to the site of blockage by viewing a real-time x-ray image of the catheter and probe in the blood vessel;

(f) extending the probe from the end of the catheter so that the probe tip makes contact with the fibrous or calcified plaque or blood clot at the site of arterial blockage; and (g) transmitting ultrasonic energy along the probe so as to vibrate the probe tip at ultrasonic frequencies in the longitudinal and transverse directions, thereby breaking up and pulverizing the fibrous or calcified plaque or blood clot.

15. The method of claim 14 wherein the step (c) of introducing the catheter carrying the probe into the blood vessel includes introducing a radiographic contrast fluid through the catheter to the site of the blockage in the blood vessel and viewing the contrast fluid in real-time on an x-ray image.

16. The method of claim 14 wherein the catheter has a plurality of internal passageways that extend along its length.

17. The method of claim 16 further including the step of:
(f) removing plaque debris from the area of the treatment site by creating a suction through one of the internal passageways of the catheter.

18. The method of claim 14 wherein the catheter has an annular balloon around its outer circumference at its second end and includes means for inflating the annular balloon; and the step (c) includes inflating the annular balloon so as to block off the treatment site and center the catheter in the blood vessel.

19. The method of claim 14 wherein the step (e) of transmitting ultrasonic energy along the probe includes pulsing the ultrasonic energy in 20 msec. cycles.

20. Apparatus as defined in claim 1 wherein the probe tip has a bulbous shape such that the tip of the probe is rounded and has a diameter greater than the diameter of the remainder of the probe.

21. Apparatus as defined in claim 6 wherein said tip has a bulbous, rounded form.

22. A method as defined in claim 7 wherein the tip has a bulbous, rounded form.

23. A method as defined in claim 14 wherein the probe tip has a bulbous shape such that the tip of the probe is rounded and has a diameter greater than that of the remainder of the probe.

24. An ultrasonic apparatus for the treatment of a patient having blood vessels obstructed by deposits of atherosclerotic plaque of blood clots, comprising:
an ultrasonic energy source;
an elongated, solid, flexible probe having first and second ends and coupled at the first end to the ultrasonic energy source and having a tip at the second end, the probe length selected so as to provide both longitudinal and transverse motion of the probe tip, the probe tip having a blunt, rounded shape formed to be substantially free of any tendency to perforate a blood vessel and the probe having a degree of flexibility selected to prevent perforation of the blood vessel upon contact with the probe tip;
a hollow catheter for internally carrying a portion of the probe, the catheter having first and second ends; and
means adapted to slide the probe within the catheter and to extend the probe from the second end of the catheter into a mass of atherosclerotic plaque or blood clots, and means to reduce and control the temperature of said tip including means connected to said source for causing said source to supply pulsed ultrasonic energy to said probe.

25. An ultrasonic apparatus for the treatment of a patient having blood vessels obstructed by deposits of atherosclerotic plaque or blood clots, comprising:
an ultrasonic energy source;
an elongated, solid, flexible probe having first and second ends and coupled at the first end to the ultrasonic energy source and having a tip at the second end, the probe length selected so as to provide both longitudinal and transverse motion of the probe tip, the probe tip having a blunt, rounded shape formed to be substantially free of any tendency to perforate a blood vessel and the probe having a degree of flexibility selected to prevent perforation of the blood vessel upon contact with the probe tip; and
a hollow catheter having first and second ends, internally carrying a portion of the probe, the second end of the probe adapted to be inserted into the blood vessel to be treated; the catheter having an inflatable annular balloon around the outer circumference of the second end of the catheter, and means to reduce and control the temperature of said tip including means connected to said source for causing said source to supply pulsed ultrasonic energy to said probe.

26. An ultrasonic apparatus for the treatment of a patient having blood vessels obstructed by deposits of atherosclerotic plaque or blood clots, comprising:
an ultrasonic energy source constituting means for producing pulsed ultrasonic vibrations;
a flexible, elongated metal wire probe having one end adapted to be coupled to the ultrasonic energy source and having a tip at the other end, and the length of the probe being selected so that the probe length is an acoustical length of a whole number multiple of a one-half wavelength of the frequency of the ultrasonic energy source in the material of which the probe is constructed, with the tip of the probe located at an antinode of the probe length, the tip having a blunt, rounded shape formed to be substantially free of any tendency to perforate a blood vessel and the probe having a degree of flexibility selected to prevent perforation of the blood vessel upon contact with the probe tip;
a hollow catheter comprised of a flexible material having an inside diameter sufficient to internally carry the blunt, rounded tip of the probe, adapted to be inserted into the blood vessel at one end, and having an inflatable cuff at the inserted end that may be inflated to axially center the catheter and probe in the blood vessel; and
means, coupled to the catheter, for introducing fluid into the blood vessel through the catheter.

27. A method of treating a patient suffering from partial or total blood vessel blockage due to the deposition of fibrous or calcified plaque or a blood clot on the blood vessel interior wall, the method comprising the steps of:
(a) providing an ultrasonic energy source; an elongated, hollow catheter; and an elongated, solid, flexible probe carried internally within the catheter;
(b) providing the probe with a blunt, rounded tip having a length that results in both longitudinal and transverse motion of the probe tip, the blunt, rounded tip being formed to be substantially free of any tendency to perforate a blood vessel and the probe having a degree of flexibility selected to prevent perforation of the blood vessel upon contact with the probe tip;
(c) attaching a first end of the catheter and probe to the ultrasonic energy source such that a second end of the probe is coextensive with a second end of the catheter;

(d) making an incision in the outer skin of the patient down to a blood vessel;

(e) angiographically introducing the catheter carrying the probe into the blood vessel and advancing the catheter and probe to the site of blockage by viewing a real-time image of the catheter and probe in the blood vessel;

(f) extending the probe from the end of the catheter and thereby making contact with the fibrous or calcified plaque or blood clot at the site of blockage; and (g) transmitting pulsed ultrasonic energy along the probe so as to vibrate the probe tip at ultrasonic frequencies in the longitudinal and transverse directions, thereby breaking up and pulverizing the blockage without overheating the probe tip.

28. A method of treating a patient suffering from partial or total blockage of a blood vessel due to the deposition of fibrous or calcified plaque or a blood clot on the blood vessel interior wall, the method comprising the steps of:

(a) providing an ultrasonic apparatus comprising an ultrasonic energy source; an elongated, solid, flexible probe coupled at a first end to the ultrasonic energy source and having a tip at a second end; a hollow catheter for internally carrying a portion of the probe such that the catheter is adapted to be coupled at a first end to means for introducing fluid into the catheter and inserted at a second end of the catheter into the blood vessel to be treated, and means to slide the probe within the catheter and to extend the probe from the second end of the catheter into a mass of atherosclerotic plaque or blood clot;

(b) providing the probe tip with a blunt, rounded shape formed to be substantially free of any tendency to perforate a blood vessel and the probe having a degree of flexibility selected to prevent perforation of the blood vessel upon contact with the probe tip, and the probe is selected to have a length that results in both longitudinal and transverse motion at the blunt, rounded tip;

(c) inserting the probe within the catheter and attaching the first end of the probe to the ultrasonic energy source such that the second end of the probe is coextensive with the second end of the catheter;

(d) mixing an incision in the outer skin of the patient down to a blood vessel and angiographically inserting a self-sealing sheath into the blood vessel;

(e) introducing the catheter carrying the probe through the self-sealing sheath and into the blood vessel, and advancing the catheter and probe to the site of blockage by viewing a real-time image of the catheter and probe in the blood vessel;

(f) extending the probe from the end of the catheter so that the probe tip makes contact with the fibrous or calcified plaque or blood clot at the site of arterial blockage; and (g) transmitting pulsed ultrasonic energy along the probe so as to vibrate the probe tip at ultrasonic frequencies in the longitudinal and transverse directions, thereby breaking up and pulverizing the fibrous or calcified plaque or blood clot without overheating the probe tip.

29. The ultrasonic apparatus of claim 24 wherein the diameter of the probe tip is slightly less than the inside diameter of the catheter.

30. The ultrasonic apparatus of claim 24 wherein the probe tip is provided with a flexible extension approximately 2 cm in length along the longitudinal axis of the probe, the extension being flexible enough to fold back on itself when contacting the blood vessel wall.

31. The ultrasonic apparatus of claim 25 wherein the catheter has a plurality of internal passageways that extend along the length of the catheter.

32. The ultrasonic apparatus of claim 25 wherein the catheter has means for inflating the balloon after the second end of the catheter is in the blood vessel.

33. The method of claim 28 wherein the step (e) of advancing the catheter and probe to the site of an arterial blockage includes introducing a radiographic contrast fluid through the catheter and around the probe to the site of the blockage in the blood vessel and viewing the contrast fluid in real-time on an x-ray image.

34. The method of claim 33 further comprising the step of:

(h) viewing the flow of contrast fluid released from the catheter into the blood vessel after the transmission of ultrasonic energy to determine the extent of destruction of the arterial blockage.

35. The method of claim 27 further comprising the step of:

(h) supplying a physiologic fluid through the catheter to the site of arterial blockage to control the temperature of the probe tip while the ultrasonic energy is being applied.

36. The method of claim 27 further comprising the step of:

(h) removing plaque debris from the area of the treatment site by creating a suction through the catheter.

37. The method of claim 27 wherein the catheter has a plurality of internal passageways extending along its length, the method further comprising the step of:

(h) removing plaque debris from the area of the treatment site by creating a suction through one of the internal passageways.

38. The method of claim 27 wherein the catheter has an annular, inflatable cuff located around the outer circumference of the second end of the catheter; and the step (f) of the method further includes inflating the annular cuff, thereby blocking off the treatment site and centering the catheter in the blood vessel.

39. The method of claim 28 wherein the step (e) of introducing the catheter carrying the probe into the blood vessel includes introducing a radiographic contrast fluid through the catheter to the site of the blockage in the blood vessel and viewing the contrast fluid in real-time on an x-ray image.

40. The method of claim 28 wherein the catheter has a plurality of internal passageways that extend along its length.

41. The method of claim 40 further including the step of:

(h) removing plaque debris from the area of the treatment site by creating a suction through one of the internal passageways of the catheter.

42. The method of claim 28 wherein the catheter has an annular balloon around its outer circumference at its second end and includes means for inflating the annular balloon; and the step (e) includes inflating the annular balloon so as to block off the treatment site and center the catheter in the blood vessel.

43. The method of claim 28 wherein the step (g) of transmitting pulsed ultrasonic energy along the probe includes pulsing the ultrasonic energy in 20 msec. cycles.

* * * * *